United States Patent [19]

Pall et al.

[11] Patent Number: 4,861,617

[45] Date of Patent: Aug. 29, 1989

[54] METHOD OF REDUCING THE ADHESION OF BUBBLES IN MEDICAL EQUIPMENT

[75] Inventors: David B. Pall, Roslyn Estates; Peter J. Degen, Huntington; Vlado I. Matkovich, Glen Cove; Thomas C. Gsell, Glen Cove, all of N.Y.

[73] Assignee: Pall Corporation, Glen Cove, N.Y.

[21] Appl. No.: 75,658

[22] Filed: Jul. 20, 1987

[51] Int. Cl.$^4$ .................... A61M 31/00; B05D 3/06
[52] U.S. Cl. .............................. 427/2; 427/36; 427/44; 427/54.1; 522/3; 604/122; 604/126; 604/265; 604/266
[58] Field of Search .................. 427/2, 44, 54.1, 36; 522/123, 3; 604/122, 126, 4, 7, 43, 44, 51, 52, 53, 54, 190, 83, 265, 266

[56] References Cited

U.S. PATENT DOCUMENTS

| | | | |
|---|---|---|---|
| 3,566,874 | 2/1971 | Shepherd et al. | 424/81 X |
| 3,695,921 | 10/1972 | Shepherd et al. | 424/81 X |
| 3,861,396 | 1/1975 | Vaillancourt et al. | 128/350 R |
| 3,939,049 | 2/1976 | Ratner et al. | 522/123 |
| 4,055,682 | 10/1977 | Merrill | 427/2 |
| 4,196,065 | 4/1980 | Gaussens et al. | 522/123 |
| 4,459,318 | 7/1984 | Hyans | 427/36 |
| 4,526,579 | 7/1985 | Ainpour | 604/265 |
| 4,527,293 | 7/1985 | Eckstein et al. | 623/12 |

*Primary Examiner*—Allan M. Lieberman
*Attorney, Agent, or Firm*—Leydig, Voit & Mayer

[57] ABSTRACT

A method of reducing the adhesion of bubbles to the surfaces of a medical administration set with which a parenteral liquid comes in contact prior to its introduction into a patient by treating the surfaces of the medical administration set with which the liquid comes in contact to increase the critical surface tension thereof prior to contacting the surfaces of the medical administration set with the liquid, preferably by radiation grafting with a solution of a monofunctional monomer compound.

6 Claims, No Drawings

METHOD OF REDUCING THE ADHESION OF BUBBLES IN MEDICAL EQUIPMENT

TECHNICAL FIELD

This invention is directed to a method for reducing the adhesion of gas bubbles of polymeric surfaces and to articles having a reduced affinity for bubbles at the articles' surfaces. More particularly, the present invention is directed to a method of treating the polymeric surfaces of medical equipment with which parenteral liquids come in contact to reduce the adhesion of bubbles thereto and thereby reduce the likelihood of introducing gas bubbles into a patient.

BACKGROUND OF THE INVENTION

In many situations in which a liquid comes in contact with a medical administration set such as a filter housing, gas-filled bubbles which cling to the surfaces of the housing may be formed as a result of gas dissolved in the liquid or which may be introduced into the liquid during the course of carrying out a particular procedure, e.g. the oxygenation of blood. In many instances, the presence of such bubbles has little effect on either the filtration process, flow properties, or downstream occurrences. However, in situations where it is desirable to maintain a constant flow rate, variations in flow caused by the generation of gas bubbles is undesirable. In other situations, the introduction of bubbles may adversely affect processes downstream of the filter housing. specifically, in medical applications when a patient is infused intravenously with parenteral fluids, the introduction of bubbles can prove life-threatening to the patient.

Various complications can arise from air bubbles in such medical apparatus. In the apparatus itself, air can block or reduce the effective surface area of a filter, thereby decreasing the efficiency of the apparatus as a whole. Also in the process of using such apparatus, there exists the inherent danger of bubbles being introduced into the patient and forming an air embolism.

Introducing air into the circulatory system of a patient can lead to serious consequences. Small amounts of air can be swept with the blood through the heart without adverse effects. However, bubbles may lodge in the small blood vessels. This can markedly increase the resistance to blood flow, and flow can be reduced or even eliminated. Blockage of small vessels in the brain may lead to serious or even fatal neurological abnormalities. Blockage of the coronary arteries can cause myocardial damage.

In addition, air which enters the venous blood may eventually clog the vessels of the lungs, resulting in diffuse pulmonary embolism. The air has a large surface tension at the interface between the blood and air so that globules of air cannot be deformed enough to be pushed along the capillaries. The physical effects of diffuse pulmonary embolism on the pulmonary circulatory system are similar to those of massive pulmonary embolism, i.e., increased pulmonary circulatory resistance with resulting increase in pulmonary arterial pressure and failure of the right side of the heart. However, with diffuse embolism, the pulmonary vessels appear to develop considerable vasospasm which adds additional resistance to flow besides that caused by the emboli themselves. Patients with this type of embolism exhibit a rapid respiratory rate because of local irritation by the emboli in the lungs and also because of resultant ischemia throughout the body.

It is therefore desirable to eliminate gas bubbles from the administration set in an expeditious manner. This is of particular concern when transparent components are used in the administration set. In such instances, users are tempted to removed entrained gas bubbles by striking the equipment with a reflex hammer. This is dangerous from the standpoint of potential leakage by virtue of a broken part, and also because of the potential to cause misfunction of the component.

Additionally, time is often of the essence for procedures in which administration of parenteral fluids is involved. Expeditious removal of adhered gas bubbles allows the timely used of said equipment in, for example, life threatening situations.

The subject invention is directed then to a method for treating medical administration sets with which parenteral liquids come in contact to reduce the adhesion of bubbles to the equipment and allowing expeditious removal by venting of these bubbles, thereby reducing the danger of introducing undesirable components into a patient and the corresponding likelihood of embolism formation.

DISCLOSURE OF THE INVENTION

In accordance with this invention, a method is provided for treating medical administration sets to reduce the danger of introducing gas bubbles into a patient. By "medical administration sets" is meant housings such as for example, filters, fitments, and the like with which a parenteral liquid comes in contact as it is conveyed from a source, e.g., a bag containing a unit of blood or an intravenous solution, to the patient. This is achieved by modifying the surface of these plastic components (such as polycarbonates, polyacrylates, polysulfones, polyesters, polystyrenes, polyacrylonitriles, polybutadienes, and copolymers thereof), preferably by radiation grafting, to increase the critical surface tension of such materials, preferably to a value approaching or exceeding the surface tension of the liquid(s) with which the surface comes in contact in the course of use.

The method of increasing the critical surface tension of the solid surface of the plastic component (thereby reducing the contact angle of liquids which come in contact with the component) preferably comprises contacting the polymeric surface of the equipment with a solution of a monofunctional reactive monomeric compound having at least one hydroxyl group [hereinafter "monomer"]. The term "monofunctional", as used herein in describing the reactive groups of the monomer which makes it suitable for use in forming a surface-grafted, surface-modified polymeric surface, refers to those functional groups which are believed to be responsible for polymerization and bonding to the polymeric surface. After contacting the polymeric surface witha solution of the monomer, the combination is exposed to ionizing radiation.

By effecting polymerization (and grafting) of the monomer at the polymeric surface, the resultant material is stable and will not leach components which could be conveyed into the patient along with the parenteral fluid, i.e., the method of treatment in accordance with the subject invention provides a permanent modification with the treated surfaces being substantially free of leachable components such as surfactants. This treatment also provides a substantially non-ionic surface to avoid the removal of charged active species within the medical liquid that could potentially adversely change the nature of the fluid.

BEST MODE FOR CARRYING OUT THE INVENTION

The polymeric surface may be comprised of a material having C-H bonds capable of forming radicals under the influence of ionizing radiation, such as polycarbonates, polyacrylates, polysulfones, polyacrylonitriles, polybutadienes, polyesters, polystyrenes, and copolymers thereof. Preferably, the polymeric surface formed from the monomer is rich in pendant hydroxyl groups or is capable of forming a plurality of pendant hydroxyl groups.

To achieve the desired reduced bubble adherence, the polymeric surface of the medical administration set, or the portions thereof with which the liquid comes in contact, are contacted with the monomer solution. Suitable solvents for this solution are alcohols, hydrocarbons, halogenated hydrocarbons, and protic and aprotic solvents; however, most preferred is deionized water. The polymer surface is then subjected to ionizing radiation (gamma, X-ray, or ultraviolet) and rinsed to remove any unreacted and unbound monomer.

This is followed by drying the polymer surface by any convenient means, for example, by a forced air oven. The adhesion of gas bubbles to the polymer surface is virtually eliminated, and the contact angle of the resultant surface by a drop of water is significantly reduced.

The solid surfaces of medical administration sets treated in accordance with the method of this invention have film break up times as defined in Example 1 of at least about 3 seconds, more preferably at least about 5 seconds.

The invention will be better understood by reference to the followng examples which are offered by way of illustration.

EXAMPLE 1

A solid housing part for a biomedical filter, comprised of Cyro XT-735 (a copolymer of methyl methacrylate, styrene butadiene, and acrylonitrile available from Cyro Corporation) was immersed in a solution containing 0.135% by volume of 2-hydroxyethylmethacrylate (HEMA) (Rocryl 400, a product of Rohm and Haas) in deionized water contained in a stainless steel vessel.

The stainless steel container was then sealed and placed in proximity to a source of cobalt-60 radiation at a radiation rate of 625,000 rads/hour for a total of about 1.5 megarads.

The plastic part was then removed from the solution, rinsed with deionized water, and dried at a temperature in the range of from about 150 to about 200° F., i.e. at a temperature below the melting point of the material but at a high enough temperature to carry out the process economically.

The contact angle of a drop of water with the virgin Cyro XT-735 material was about 70°–80°. After treatment, the contact angle of a drop of water with the treated surface was about 45°–55°.

Thereafter, the part was immersed in a beaker of pure water following which the part was withdrawn from the beaker of water by hand within one second and the time required for the film of water on the part to be visually observed to break was recorded. The untreated material had a timed breakup of the film of about 1 second, contrasted with the treated material which was on the order of 10 seconds to 3 minutes.

EXAMPLE 2

A plastic filter housing, comprised of RSA 3G, a copolymer of methyl methacrylate-styrenebutylacrylate-butadiene blend available from Richardson Plastics Corporation, was treated in the same manner as described in example 1, except that the concentration of HEMA was 0.1% by volume.

Following the treatment and subsequent drying, the part was found to have a water contact angle of 29°, and held a film of water for 3 seconds.

An untreated part of the same material for comparison purposes had a water contact angle of 42°, and did not support a water film for any measurable time period.

EXAMPLE 3

A 0.010" thick polypropylene mesh obtained from Nalle Plastics, that is a component of a biomedical filter, was treated in the same manner as described in Example 1. The water contact angle of the treated mesh was 25°, whereas an untreated control mesh had a water contact angle of 65°.

We claim:

1. A method of reducing the adhesion bubbles to the polymeric surfaces of a medical administration set with which a parenteral liquid comes in contact prior to its introduction into a patient, comprising treating said polymeric surfaces of the medical administration set with which the liquid comes in contact to increase the critical surface tension thereof prior to contacting the polymeric surfaces of the medical administration set with the liquid wherein said treatment comprises:
    contacting said polymeric surface with a solution of a monofunctional reactive monomer compound having at least one hydroxyl group, and
    exposing said polymeric surface and said monomer compound to ionizing radiation to effect polymerization of said monomer compound and grafting at the polymeric surface.

2. The method of claim 1 wherein said polymeric surface comprises a material having C-H bonds capable of forming radicals under the influence of ionizing radiation.

3. The method of claim 1 wherein said polymeric surface is selected from the group consisting of polycarbonates, polyacrylates, polysulfones, polyacrylonitriles, polybutadienes, polyesters, polystyrenes, and copolymers thereof.

4. The method of claim 1 wherein said modified polymeric surface formed from said monomer compound is rich in pendant hydroxyl groups.

5. The method of claim 1 wherein said modified polymeric surface formed from said monomer compound is capable of forming a plurality of pendant hydroxyl groups.

6. The method of claim 1 wherein said monomer compound comprises an ethylenically unsaturated compound.

* * * * *